(12) United States Patent
Diehn et al.

(10) Patent No.: US 7,411,112 B2
(45) Date of Patent: Aug. 12, 2008

(54) MAIZE PROMOTER NAMED CRWAQ81

(75) Inventors: Scott Diehn, West Des Moines, IA (US);
Albert Laurence Lu, Newark, DE (US);
Steven W. Ritchie, Omaha, NE (US);
Lynne Sims, Polk City, IA (US); Kim R. Ward, Bear, DE (US); Philip Benfey, Chapel Hill, NC (US); Jee W. Jung, Durham, NC (US)

(73) Assignees: Pioneer Hi-Bred International, Inc., Johnston, IA (US); E.I. du Pont de Nemours and Company, Wilmington, DE (US); New York University, New York, NY (US)

( * ) Notice: Subject to any disclaimer, the term of this patent is extended or adjusted under 35 U.S.C. 154(b) by 489 days.

(21) Appl. No.: 10/961,629

(22) Filed: Oct. 8, 2004

(65) Prior Publication Data

US 2005/0097633 A1    May 5, 2005

Related U.S. Application Data

(60) Provisional application No. 60/509,878, filed on Oct. 9, 2003.

(51) Int. Cl.
*C12N 15/82* (2006.01)
*A01H 5/00* (2006.01)
*C07H 21/04* (2006.01)

(52) U.S. Cl. ............... 800/287; 800/298; 536/24.1; 435/320.1; 435/468; 435/419

(58) Field of Classification Search ............ None
See application file for complete search history.

(56) References Cited

U.S. PATENT DOCUMENTS

| | | | |
|---|---|---|---|
| 6,686,513 B1 | 2/2004 | Albert et al. | |
| 7,205,454 B2 * | 4/2007 | Vanderkimpen et al. | .... 800/287 |
| 2004/0019934 A1 | 1/2004 | Ekramoddoullah et al. | |

FOREIGN PATENT DOCUMENTS

| | | |
|---|---|---|
| EP | 0452 269 A2 | 10/1991 |
| EP | 1 385 964 A2 | 11/2002 |
| WO | WO 98/22593 | 5/1998 |
| WO | WO 00/31249 A1 | 6/2000 |
| WO | WO 01/00833 A1 | 1/2001 |
| WO | WO 02/40687 A3 | 5/2002 |
| WO | WO 02/46439 A2 | 6/2002 |
| WO | WO 2004/013169 A1 | 2/2004 |

OTHER PUBLICATIONS

Donald et al. Mutation of either G box or I box sequences profoundly affects expression from the Arabidopsis rbcS-1A promoter. (1990) The EMBO Journal, vol. 9, pp. 1717-1726.*
Benfey et al. The cauliflower mosaic virus 35S promoter: combinatorial regulation of transcription in plants. (1990) Science, vol. 250, pp. 959-966.*
Kim et al. A 20 nucleotide upstream element is essential for the nopaline synthase (nos) promoter activity. (1994) PMB; vol. 24, pp. 105-117.*
Rabinowicz et al. Genomic shotgun sequences from Zea mays (methyl-filtered); ia80g10.b1WGS-ZmaysF (JM107 adapted methyl filtered) Zea mays genomic clone ia80g10 5', genomic survey sequence. (2002) GenBank Accession BZ317130, pp. 1-2.*
Whitelaw et al. Maize Genomics Consortium, PUBJQ08TD ZM_0.6_1.0_KB Zea mays genomic clone ZMMBTa070B15. (2003) GenBank Accession BZ671913, pp. 1-2.*
NCBI Database Report for Accession No. X61085, Jul. 25, 1991.
NCBI Database Report for Accession No. X73152, May 18, 1993.
Derwent Database Report for Accession No. AAV32438, Oct. 18, 1998.
Database EMBL, Accession No. BZ671913, Feb. 6, 2003 (XP-002313156).
Database EMBL, Accession NO. ZMAZ22KD, Aug. 15, 1991 (XP-002313157).
Database EMBL, Accession No. ZMGAPC4, Jun. 16, 1993 (XP-002313158).

* cited by examiner

*Primary Examiner*—Cynthia Collins
*Assistant Examiner*—Cathy Kingdon Worley
(74) *Attorney, Agent, or Firm*—Alston & Bird LLP

(57) ABSTRACT

The present invention provides compositions and methods for regulating expression of heterologous nucleotide sequences in a plant. Compositions include a novel nucleotide sequence for a root-preferred promoter for the gene encoding CRWAQ81. A method for expressing a heterologous nucleotide sequence in a plant using the promoter sequences disclosed herein is provided. The method comprises stably incorporating into the genome of a plant cell a nucleotide sequence operably linked to the root-preferred promoter of the present invention and regenerating a stably transformed plant that expresses the nucleotide sequence.

36 Claims, 3 Drawing Sheets

```
   1   ATCGGAGCCG CTCGGCAGGG ATCTGGAATG GTTCAGGCAG CAAGGTCACG
  51   TAGTTCTGGA ACCATCTGGG CATTGCGTAC GCTTCCTTTC TGGTAGAGCT
 101   ATCTGAGAAG AACCCCCCGG CGTTTGTTTG CCATTTCTAC TACGTGTACT
 151   TCGCTCATGC TGCCGGAGGC CGAATCATCG TCAAAAAAGG TGATGAACTA
 201   ACTGATTATG AGTGTGTTAT GTCTGAAAAC CATATGAACG AAGAACTAAT
 251   TTGTAAGATC ATTTGTTTAT GATCTATTTA CAATGATCTA TTTACCATGA
 301   TCTGTTTACA ACTAGCAGGA GGTGTTTACC ATGATCTGTT TACAATCATA
 351   TGAACTAATT ACAACTAGCA TGGTAACACA AGCTCCTGTT TAATTCAGAT
 401   TATTGTAATT CATAGTCATT TTTCTCTAAT GGTAAGTTGC TATGGTTGTA
 451   AATCATATCC AAATGATTGT AATTAGTTTA ATTTATGTTT CAAAATCATA
 501   TTTTTAGTTC AAATCTGTTG TAATTCATCA GAAGGATCTG TTTACAATGT
 551   TCATGGTCAT TTTTCTGTAC TGGTAAGTTG CTCCTACTGT ATCTGTATCC
 601   CTTATGGGGT ATTACAAAGG ATCTGTTGTA ATTTTTCTGT ACTGGTAAGT
 651   TGCTCCTACT GTATCTGTAT GTGTAAGTTG CTCCTACTGT ACAGAGACCC
 701   AGAGACCTGA TGGGGTATTT TTCAAAATCT GTTGTAATCT ATGGGTGTAA
 751   ATCATATTTA GATGATTGTA ATTAGTTCAA TTTATAGGTC AAAATCATAT
 801   TTTTAGTTCA AAACTGTTGT AATTTGTTTA ATAACGTTTA AAATTTTGAA
 851   ATTTGGCGAG AACTGTATCT AACACATCAA AATTGGCGGT AACCCAATTG
 901   GGCCAAGCTA AAAAAAATGA GAACCAAACA ATGTGTTATA TGGGCCAGGT
 951   TTATTTTGAC CAGGCAACCA AACATTTTAG GTTGGCTCAT TATATACGGG
1001   CTCCCTTGAG CCTGGTTCTC TCACTGAGCC AGGCTCAGGC TGGACCAGGC
1051   AACCAAACAT ATCCTTAGGT GCTGCTCGTC TCCACACCTC CTCTGGCCTT
1101   GTTGAGCACT AAAAAGTGCC ATGTTTGACA TTTTATTGGG ACCTCATCTA
1151   TCCTCACCGC AAGGAGAAAA GCCTACATGG GAGGGGATGG ATCGGCCTTG
1201   TAGAAGGGAT ATCTCATACA GTACAAGGTG CCTTGACTAC TGAAGACAAG
1251   TTATCAACTA GATATGCTTA GAAGCCAAGT AACTTGGCAA GATCCCCTTG
1301   GATATGACTA GATTTCCTTA TAACCAACTA GGAAACTTTG TCTTAAGGTC
1351   GATTAGGATT TAGGACTCCA TGGGCAACCT ATTCTATGGG CTATATGAGG
1401   AGGGATATAT AGGGGACCCC TAACTGACAT ATTCCACACA ACTCATCATA
1451   GAAACTTTCT GCACTATAAC TAGAATCCAA CGACCCTGTA ACTCGAGTGC
1501   ATATCACAAA GAGAAGCTTT CTGCACTGGA GGTAGTGTAC TTTGTACTTG
1551   AAACTTATAT AAATTTGTGC CTTTTATACT CCATCGTTCG AAAATATAGT
1601   ACTTTTTTGT CTCTTTTTTC GTCCACTCAT TGGAATGATA ATAAATATAG
1651   ACATACATAA CAACTATATT TATAGGTTAA TTAATAAATA TATATTTAGT
1701   GTAAACAAA ATATATTTTA CCCATTTTAT TCCTTATGCA TGAAACGTTG
1751   ATCTACTTGT CAGATGGAAA AATACTACGA CGTTGTTGTA CCAGACCGCA
1801   CCTAAATCAA ACTGTTTTCA GAGATGGCCA TTCTATTATT GTAGATTTGT
1851   GATACCATGT ACTTTTTTAT CCATAAAATA CCATACCATT ATGATATGGA
1901   TATCTTCATC AGACCGACTC ATTATCTCTC TCTCTATATA TATAAACACC
1951   TATATATCAA ACAGGCATAA AGAAAAACA GATGATTTTT TTCTGAAGT
2001   AGACTGACAG AAGCAGAAGT GTGAGTCTTT TGTTTCAAT TTTATAATGT
2051   GTAAAGAAAA TGACGCCAAT GAAATATGTG TCTGGGCTGA CGTGTTGTTT
2101   CGTGAAAGCC AATTTTGTTG TATATACGGG GGCCACAGCC CAGTTGTATT
2151   TGTTGCCGGG ACTGGCGCAA AAAAAATCC CCTTGGATAT GACTAGATTT
```

FIG. 2A

```
2201  CCTTATAACG AACTAGGAAC TTCATGTTAA GGTCGATTAG GATTTAGGAC
2251  TCCATCGGCA ATCTATTCTA CGGGCTATAT GAGGAGGGAT AGGGGTCCCC
2301  TAAGTGACAT TCCACACAAC TCATCATAGA ACTAGAATCC AACGGCCTGT
2351  AACCCAAGTG CATAGCATAA AGAGAAGCTT TCTGCACTGG ATGTAGTGTA
2401  ctttatactt gaaacttgta taaatttgtg tcttttatac tccctcagtt
2451  tgaaatatag ttctttctag cctcttttt tccgtccaca ctcatttgaa
2501  tgataataaa tatagatata catacaaact atattcatag gttaattaat
2551  aaatgtatat ttagtctaaa atgaaatata ttttacccat cgtattcctt
2601  atgcatgaaa tgttgatcta cttgtctgat ggaaaaatac tacgacgttg
2651  ttgtaccaga ccgcacctaa atcaaactgt tttcagagat ggccattcta
2701  ttattgtaga tttgtgatac gtacgatgta ctttttatc cataaaatac
2751  cgtaccatta tgatatggat atcttgatga gagggactca ttatctctct
2801  ctatatatat aaacacctat atatcaaaca ggcatcaaga aaaatagatg
2851  atttttttt ctgaagtaga gtgacagaag cagctgaagt gtgagtcttt
2901  ttgtttcaat tttataatgt gtaaagaaaa tgacgccaat gaaatatgtg
2951  tctgggctga cgtgttgttt ggtgaaagcc aattttgttg tatatagggg
3001  ggccagagcc cagttgtatt tgatgcccgg actggcgcca aaaaaaaatc
3051  CGGATAGTAC TATTCCGCTA ACTGTGTCAC ACTTTATCTA AAATTAGTCA
3101  tccaaattaa agaactaacc ttagatacaa aaaattaaac aaagtatgac
3151  AAGTTAGGTA GCAAACTAAA CTAAAGAGGA TAACACAACA GTTAACCGTC
3201  GACGTGCGCG GCCTGAATTT ACTACTACAG ATAACACGAC AGTTAACGAG
3251  CGGGTATGGG TTGTCTTCCT TGAGCACTGT TGTTCTCTAG AATCTCTGAA
3301  TCTCTCTCTG TCTTGATGAC ACCGAGCGGA AATAGCAGTT GGAAGAGGTG
3351  ATTGGGCTTC AGCGCGCGAT CCAACCCAAG TGGGTTCCAC AACGTGAACC
3401  TCATGCAGCT TAAAATACAG CCAGTTGTGA TCCATCTGCC ACAGCTGTTT
3451  CTACCTCAGA TGTGCTACAC AGTGTATTAC CTGTTTCTAC CTCGCAGATG
3501  TGCTACACAG TTGCTTATGA CTGCCTATAA AATGGCCGGG ATCGGTGAGG
3551  CTGCTGGaac caaggagaga gagcatatat atc
```

FIG. 2B

SEQUENCE LISTING

```
<160> NUMBER OF SEQ ID NOS: 2

<210> SEQ ID NO 1
<211> LENGTH: 2136
<212> TYPE: DNA
<213> ORGANISM: Zea mays
<220> FEATURE:
<221> NAME/KEY: misc_feature
<222> LOCATION: (0)...(0)
<223> OTHER INFORMATION: CRWAQ81 promoter

<400> SEQUENCE: 1
tcatcataga aactttctgc actataacta gaatccaacg accctgtaac tcgagtgcat      60
atcacaaaga gaagctttct gcactggacg tagtgtactt tgtacttgaa acttatataa    120
atttgtgcct tttatactcc atcgttcgaa aatatagtac ttttttgtct ctttttcgc     180 cactcattcg aatgataata aatatagaca tacataacaa ctatatttat aggttaatta    240
ataaatatat atttagtcta aaacaaaata tattttaccc attttattcc ttatgcatga    300
aacgttgatc tacttgtcag atggaaaaat actacgacgt tgttgtacca gaccgcacct    360
aaatcaaact gttttcagag atggccattc tattattgta gatttgtgat cgatgtactt    420
ttttatccat aaaataccat accattatga tatggatatc ttgatgagag ggactcatta    480
tctctctctc tatatatata aaccctatat atcaaacagg cataaagaaa aaacagatga    540 ttttttttctg aagtagagtg acagaagcag aagtgtgagt cttttttgttt caattttata    600 atgtgtaaag aaaatgacgc caatgaaata tgtgtctggg ctgacgtgtt gtttggtgaa    660
agccaatttt gttgtatata gggggccag agcccagttg tatttgttgc cgggactggc    720
gcaaaaaaaa atcccttgg atatgactag atttccttat aacgaactag gaacttcatg    780
ttaaggtcga ttaggattta ggactccatc ggcaatctat tctacgggct atatgaggag    840
ggataggggt cccctaagtg acattccaca catctcatca tagaactaga atccaacggc    900
ctgtaaccca agtgcatagc ataaagagaa gctttctgca ctggatgtag tgtactttat    960
acttgaaact tgtataaatt tgtgtctttt atactccctc agtttgaaat atagttcttt   1020
ctagcctctt ttttccgcca cactcatttg aatgataata aatatagata tacatacaaa   1080
ctatattcat aggttaatta ataaatgtat atttagtcta aaatgaaata tatttaccca   1140
tcgtattcct tatgcatgaa atgttgatct acttgtctga tggaaaaata ctacgacgtt   1200
gttgtaccag accgcaccta aatcaaactg ttttcagagg tggccattct attattgtag   1260
```

-continued

| | |
|---|---|
| atttgtgata cgtacgatgt acttttttat ccataaaata ccgtaccatt atgatatgga | 1320 |
| tatcttgatg agagggactc attatctctc tctatatata taaacaccta tatatcaaac | 1380 |
| aggcatcaag aaaaatagat gattttttct tctgaagtag agtgacagaa gcagctgaag | 1440 |
| tgcgagtctt tttgtttcaa ttttataatg tgtaaagaaa atgacgccaa tgaaatatgt | 1500 |
| gtctgggctg acgtgttgtt tggtgaaagc caattttgtt gtatataggg gggccagagc | 1560 |
| ccagttgtat ttgttgcccg gactggcgcc aaaaaaaaaa atccggatag tactattccg | 1620 |
| ctaactgtgt cacactttat ctaaaattag tcatccaaat taaagaacta accttagata | 1680 |
| caaaaaatta aacaaagtat gacaagttag gtagcaaact aaactaaaga ggataacaca | 1740 |
| acagttaacc gtcgacgtgc gcggcctgaa tttactacta cagataacac gacagttaac | 1800 |
| gagcgggtat gggttgtttt ccttgagcac tgttgttctc tagaatctct gaatctctct | 1860 |
| ctgtcttgat gacaccgagc ggaaatagca gttggaagag gtgattgggc ttcagcgcgc | 1920 |
| gatccaaccc aagtgggttc cacaacgtga acctcatgca gcttaaaata cagccagttg | 1980 |
| tgatccatct gccacagctg tttctacctc agatgtgcta cacagtgtat acctgtttc | 2040 |
| tacctcgcag atgtgctaca cagttgctta tgactgccta taaaatggcc gggatcggtg | 2100 |
| aggctgctgg aaccaaggag agagagcata tatatc | 2136 |

<210> SEQ ID NO 2
<211> LENGTH: 3583
<212> TYPE: DNA
<213> ORGANISM: Zea mays

<400> SEQUENCE: 2

| | |
|---|---|
| atcggagccg ctcggcaggg atctggaatg gttcaggcag caaggtcacg tagttctgga | 60 |
| accatctggg cattgcgtac gcttcctttc tggtagagct atctgagaag aaccccccgg | 120 |
| cgtttgtttg ccatttctac tacgtgtact tcgctcatgc tgccggaggc cgaatcatcg | 180 |
| tcaaaaaagg tgatgaacta actgattatg agtgtgttat gtctgaaaac catatgaacg | 240 |
| aagaactaat ttgtaagatc atttgtttat gatctatttta caatgatcta tttaccatga | 300 |
| tctgtttaca actagcagga ggtgtttacc atgatctgtt tacaatcata tgaactaatt | 360 |
| acaactagca tggtaacaca agctcctgtt taattcagat tattgtaatt catagtcatt | 420 |
| tttctctaat ggtaagttgc tatggttgta aatcatatcc aaatgattgt aattagttta | 480 |
| atttatgttt caaaatcata ttttagttc aaatctgttg taattcatca gaaggatctg | 540 |
| tttacaatgt tcatggtcat ttttctgtac tggtaagttg ctcctactgt atctgtatcc | 600 |
| cttatggggt attacaaagg atctgttgta attttctgt actggtaagt tgctcctact | 660 |
| gtatctgtat gtgtaagttg ctcctactgt acagagaccc agagacctga tggggtatt | 720 |
| ttcaaaatct gttgtaatct atgggtgtaa atcatattta gatgattgta attagttcaa | 780 |
| tttataggtc aaaatcatat ttttagttca aaactgttga aatttgttta ataacgttta | 840 |
| aaatttgaa atttggcgag aactgtatct aacacatcaa aattggcggt aacccaattg | 900 |
| ggccaagcta aaaaaaatga gaaccaaaca atgtgttata tgggccaggt ttattttgac | 960 |
| caggcaacca acattttag gttggctcat tatatacggg ctcccttgag cctggttctc | 1020 |
| tcactgagcg aggctcaggc tggaccaggc aaccaaacat atccttaggt gctgctcgtc | 1080 |
| tccacacctc ctctggcctt gttgagcact aaaaagtgcc atgtttgaca ttttattggg | 1140 |
| acctcatcta tcctcaccgc aaggagaaaa gcctacatgg gaggggatgg atcggccttg | 1200 |
| tagaagggat atctcataca gtacaaggtg ccttgactac tgaagacaag ttatcaacta | 1260 |

```
gatatgctta gaagccaagt aacttggcaa gatcccttg gatatgacta gatttcctta    1320
taaccaacta ggaaactttg tcttaaggtc gattaggatt taggactcca tgggcaacct    1380
attctatggg ctatatgagg agggatatat aggggacccc taactgacat attccacaca    1440
actcatcata gaaactttct gcactataac tagaatccaa cgaccctgta actcgagtgc    1500
atatcacaaa gagaagcttt ctgcactgga cgtagtgtac tttgtacttg aaacttatat    1560
aaatttgtgc cttttatact ccatcgttcg aaaatatagt acttttttgt ctcttttttc    1620
gtccactcat tcgaatgata ataaatatag acatacataa caactatatt tataggttaa    1680
ttaataaata tatatttagt ctaaaacaaa atatatttta cccattttat tccttatgca    1740
tgaaacgttg atctacttgt cagatggaaa aatactacga cgttgttgta ccagaccgca    1800
cctaaatcaa actgttttca gagatggcca ttctattatt gtagatttgt gatacgatgt    1860
acttttttat ccataaaata ccataccatt atgatatgga tatcttgatg agagggactc    1920
attatctctc tctctatata tataaacacc tatatatcaa acaggcataa agaaaaaaca    1980
gatgattttt tttctgaagt agagtgacag aagcagaagt gtgagtcttt ttgtttcaat    2040
tttataatgt gtaaagaaaa tgacgccaat gaaatatgtg tctgggctga cgtgttgttt    2100
ggtgaaagcc aattttgttg tatataggggg ggccagagcc cagttgtatt tgttgccggg    2160
actggcgcaa aaaaaaatcc ccttggatat gactagattt ccttataacg aactaggaac    2220
ttcatgttaa ggtcgattag gatttaggac tccatcggca atctattcta cgggctatat    2280
gaggagggat aggggtcccc taagtgacat tccacacaac tcatcataga actagaatcc    2340
aacggcctgt aacccaagtg catagcataa agagaagctt tctgcactgg atgtagtgta    2400
ctttatactt gaaacttgta taaatttgtg tcttttatac tccctcagtt tgaaatatag    2460
ttctttctag cctctttttt tccgtccaca ctcatttgaa tgataataaa tatagatata    2520
catacaaact atattcatag gttaattaat aaatgtatat ttagtctaaa atgaaatata    2580
ttttacccat cgtattcctt atgcatgaaa tgttgatcta cttgtctgat ggaaaaatac    2640
tacgacgttg ttgtaccaga ccgcacctaa atcaaactgt tttcagagat ggccattcta    2700
ttattgtaga tttgtgatac gtacgatgta ctttttttatc cataaaatac cgtaccatta    2760
tgatatggat atcttgatga gagggactca ttatctctct ctatatatat aaacacctat    2820
atatcaaaca ggcatcaaga aaaatagatg attttttttt ctgaagtaga gtgacagaag    2880
cagctgaagt gtgagtcttt ttgtttcaat tttataatgt gtaaagaaaa tgacgccaat    2940
gaaatatgtg tctgggctga cgtgttgttt ggtgaaagcc aattttgttg tatataggggg    3000 ggccagagcc cagttgtatt tgatgccggg actggcgcca aaaaaaaatc cggatagtac    3060
tattccgcta actgtgtcac actttatcta aaattagtca tccaaattaa agaactaacc    3120
ttagatacaa aaaattaaac aaagtatgac aagttaggta gcaaactaaa ctaaagagga    3180
taacacaaca gttaaccgtc gacgtgcgcg gcctgaattt actactacag ataacacgac    3240
agttaacgag cgggtatggg ttgtcttcct tgagcactgt tgttctctag aatctctgaa    3300
tctctctctg tcttgatgac accgagcgga aatagcagtt ggaagaggtg attgggcttc    3360
agcgcgcgat ccaacccaag tgggttccac aacgtgaacc tcatgcagct taaaatacag    3420
ccagttgtga tccatctgcc acagctgttt ctacctcaga tgtgctacac agtgtattac    3480
ctgtttctac ctcgcagatg tgctacacag ttgcttatga ctgcctataa aatggccggg    3540
atcggtgagg ctgctggaac caaggagaga gagcatatat atc                      3583
```

MAIZE PROMOTER NAMED CRWAQ81

CROSS-REFERENCE TO OTHER APPLICATIONS

This application claims priority to U.S. Provisional Application Ser. No. 60/509,878, filed Oct. 9, 2003, the contents of which are hereby incorporated in their entirety by reference herein.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably linked promoter that is functional within the plant host. The type of promoter sequence chosen is based on when and where within the organism expression of the heterologous DNA is desired. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized. Additional regulatory sequences upstream and/or downstream from a core promoter sequence may be included in expression constructs of transformation vectors to bring about varying levels of expression of heterologous nucleotide sequences in a transgenic plant. Genetically altering plants through the use of genetic engineering techniques to produce plants with useful traits thus requires the availability of a variety of promoters.

Frequently it is desirable to express a DNA sequence in particular tissues or organs of a plant. For example, increased resistance of a plant to infection by soil- and/or air-borne pathogens might be accomplished by genetic manipulation of the plant's genome to comprise a tissue-preferred promoter operably linked to a heterologous pathogen-resistance gene such that pathogen-resistance proteins are produced in the desired plant tissue.

Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

To date, the regulation of gene expression in plant roots has not been adequately studied despite the root's importance to plant development. To some degree this is attributable to a lack of readily available, root-specific biochemical functions whose genes may be cloned, studied, and manipulated. Several genes that are preferentially expressed in plant root tissues have been identified. See, for example, Takahashi et al. (1991) *Plant J.* 1:327-332; Takahashi et al. (1990) *Proc. Natl. Acad. Sci. USA* 87:8013-8016; Hertig et al. (1991) *Plant Mol Biol.* 16:171-174; Xu et al. (1995) *Plant Mol. Biol.* 27:237-248; Capone et al. (1994) *Plant Mol. Biol.* 25:681-691; Masuda et al. (1999) *Plant Cell Physiol.* 40(11):1177-81; Luschnig et al. (1998) *Genes Dev.* 12(14):2175-87; Goddemeier et al. (1998) *Plant Mol. Biol.* 36(5):799-802; and Yamamoto et al. (1991) *Plant Cell* 3(4):371-82. Though root-specific promoters have been characterized in several types of plants, no root-specific promoters from maize have been described in the literature.

Constitutive expression of some heterologous proteins, such as insecticides, leads to undesirable phenotypic and agronomic effects. Limiting expression of insecticidal proteins, for example, to the target tissues of insect feeding (root, in this case), allows the plant to devote more energy to normal growth rather than toward expression of the protein throughout the plant. Using root-preferred promoters, one can also limit expression of the protein in undesirable portions of the plant. However, many of the root-preferred promoters that have been isolated do not direct the expression of sufficient amounts of a transgene for efficacy in plants. Thus, the isolation and characterization of tissue-preferred, particularly root-preferred, promoters that can direct transcription of a sufficiently high level of a desired heterologous nucleotide sequence is needed.

SUMMARY OF THE INVENTION

Compositions and methods for regulating gene expression in a plant are provided. Compositions comprise novel nucleotide sequences for a promoter that initiates transcription in a root-preferred manner. More particularly, transcriptional initiation regions isolated from the plant gene CRWAQ81 are provided. Further compositions of the invention comprise the nucleotide sequence set forth in SEQ ID NO:1, the nucleotide sequence set forth in SEQ ID NO: 2 and the plant promoter sequences deposited in bacterial hosts as Patent Deposit No. PTA-5126, and fragments thereof. The compositions of the invention further comprise nucleotide sequences having at least 80% sequence identity to the sequence set forth in SEQ ID NO:1 or 2, and which drive root-preferred expression of an operably linked nucleotide sequence. Also included are nucleotide sequences that hybridize under stringent conditions to either the sequence set forth as SEQ ID NO:1 or the sequence set forth as SEQ ID NO: 2, plant promoter sequences deposited in bacterial hosts as Patent Deposit No. PTA-5126, or their complements.

Compositions of the present invention also include expression cassettes comprising a promoter of the invention operably linked to a heterologous nucleotide sequence of interest. The invention further provides expression vectors, and plants or plant cells having stably incorporated into their genomes an expression cassette mentioned above. Additionally, compositions include transgenic seed of such plants.

Methods of the invention comprise a means for selectively expressing a nucleotide sequence in a plant root, comprising transforming a plant cell with an expression cassette, and regenerating a transformed plant from said plant cell, said expression cassette comprising a promoter and a heterologous nucleotide sequence operably linked to said promoter, wherein said promoter initiates root-preferred transcription of said nucleotide sequence in a plant cell. In this manner, the promoter sequences are useful for controlling the expression of operably linked coding sequences in a root-preferred manner.

Downstream from and under the transcriptional initiation regulation of the promoter will be a sequence of interest that will provide for modification of the phenotype of the plant. Such modification includes modulating the production of an endogenous product, as to amount, relative distribution, or the like, or production of an exogenous expression product to provide for a useful function or product in the plant. For example, a heterologous nucleotide sequence that encodes a gene product that confers herbicide, salt, drought, cold, pathogen or insect resistance is encompassed.

BRIEF DESCRIPTION OF THE DRAWINGS

FIG. 1B shows northern blot analysis of the tissue-specific expression pattern of the CRWAQ81 gene in non-infested maize plants, or in maize plants infested with Western Corn Rootworm (WCRW) eggs.

FIGS. 2A and B reveal various features of the ~3.6 kb CRWAQ81 promoter sequence (SEQ ID NO:2) The nonperfect tandem repeats are highlighted. MITE1 is identified by the underlined sequence while italics identify MITE2. The bolded and underlined sequence denotes MITE3. The putative TATA box is indicated by a box. The 5' untranslated region is shown in small case lettering. SEQ ID NO:1, which is a fragment of the CRWAQ81 promoter sequence extends from nucleotide 1443 to nucleotide 3583.

DETAILED DESCRIPTION OF THE INVENTION

Figure 1:
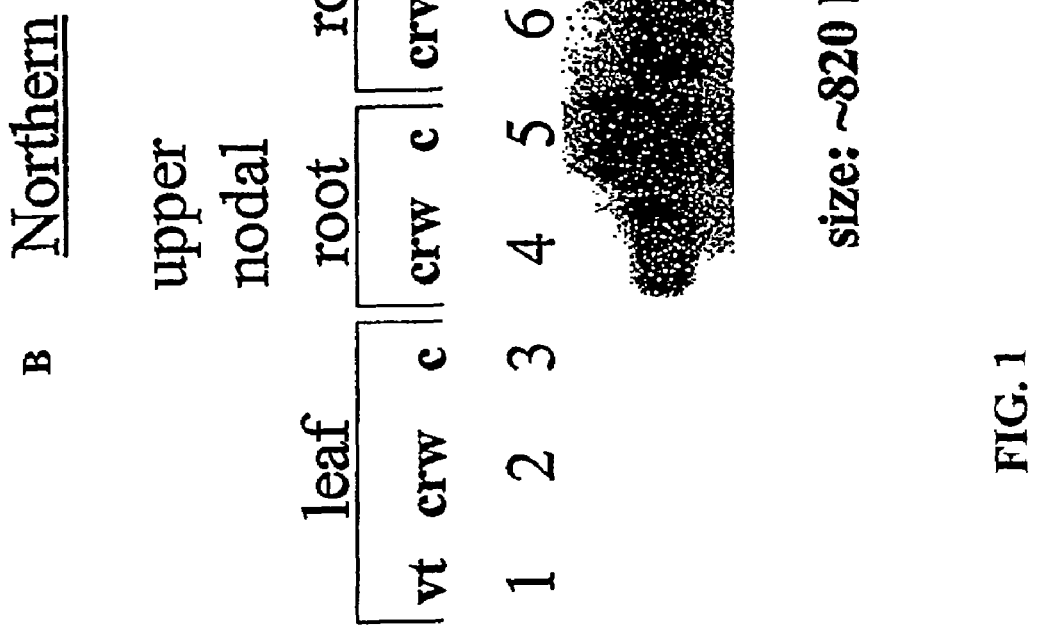
FIG. 1 shows in situ hybridization results of the expression pattern of the CRWAQ81 gene in maize root tips.
Figure 1:
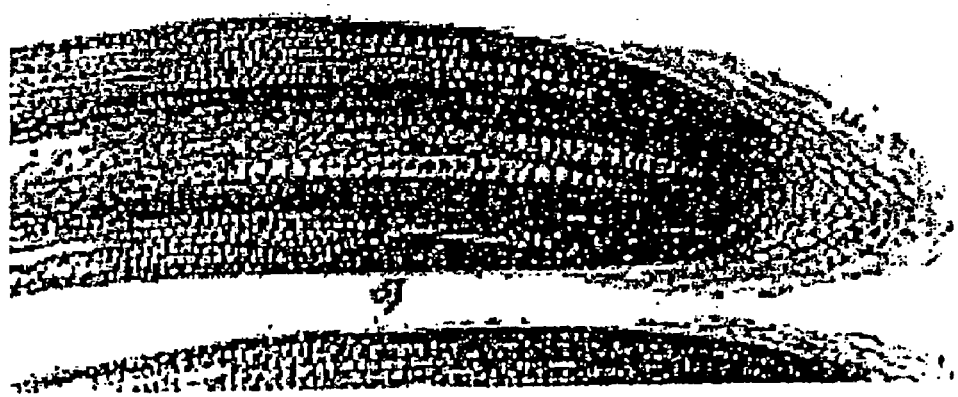

The compositions of the present invention comprise novel nucleotide sequences for plant promoters, particularly a "root-preferred" promoter for the CRWAQ81 gene, more particularly, the maize CRWAQ81 promoter. In particular, the present invention provides for isolated nucleic acid molecules comprising the nucleotide sequence set forth in SEQ ID NO:1 and the nucleotide sequence set forth in SEQ ID NO:2, plant promoter sequences deposited in bacterial hosts as Patent Deposit No. PTA-5126, and fragments, variants, and complements thereof.

Plasmids containing the plant promoter nucleotide sequences of the invention were deposited with the Patent Depository of the American Type Culture Collection (ATCC), Manassas, Va., on Apr. 4, 2003, and assigned Patent Deposit No. PTA-5126. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The promoter sequences of the invention are useful for expressing operably linked nucleotide sequences in a tissue-preferred, particularly a root-preferred manner. The sequences of the invention also find use in the construction of expression vectors for subsequent transformation into plants of interest, as probes for the isolation of other CRWAQ81-like genes, as molecular markers, and the like.

The CRWAQ81 promoter of the invention was isolated from the 5' untranslated region flanking the CRWAQ81 transcription initiation site. The specific method used to obtain the CRWAQ81 promoter of the present invention is described in Example 5 below.

The articles "a" and "an" are used herein to refer to one or more than one (i.e., to at least one) of the grammatical object of the article. By way of example, "an element" means one or more elements.

The invention encompasses isolated or substantially purified nucleic acid compositions. An "isolated" or "substantially purified" nucleic acid molecule, or biologically active portion thereof, is substantially free of other cellular material, or culture medium when produced by recombinant techniques, or substantially free of chemical precursors or other chemicals when chemically synthesized. Optimally, an "isolated" nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The compositions of the invention include isolated nucleic acid molecules comprising the promoter nucleotide sequences set forth in SEQ ID NOS:1 and 2. By "promoter" is intended to mean a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Thus, for example, the promoter regions disclosed herein may further comprise upstream regulatory elements such as those responsible for tissue and temporal expression of the coding sequence, enhancers, and the like. See particularly, Australian Patent No. AU-A-77751/94 and U.S. Pat. Nos. 5,466,785 and 5,635,618.

In the same manner, the promoter elements that enable expression in the desired tissue such as the root, can be identified, isolated, and used with other core promoters to confer root-preferred expression. In this aspect of the invention, a "core promoter" is a promoter without promoter elements. The core promoter region contains a TATA box and often an initiator element as well as the initiation site. The precise length of the core promoter region is not fixed but is usually easily recognizable. Such a region is normally present, with some variation, in most promoters. The base sequences lying between the various well-characterized elements appear to be of lesser importance. The core promoter region is often referred to as a minimal promoter region because it is functional on its own to promote a basal level of transcription.

The maize root-preferred promoter sequences of the present invention, when assembled within a DNA construct such that the promoter is operably linked to a nucleotide sequence of interest, enables expression of the nucleotide sequence in the cells of a plant stably transformed with this DNA construct. "Operably linked" is intended to mean a functional linkage between two or more elements. For example, an operable linkage between a promoter of the present invention and a heterologous nucleotide of interest is a functional link that allows for expression of the heterologous nucleotide sequence of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the heterologous nucleotide sequence of interest to be under the transcriptional regulation of the regulatory regions. The expression cassette may additionally contain selectable marker genes.

In this manner, the nucleotide sequences for the promoters of the invention are provided in expression cassettes along with a nucleotide sequence of interest, typically a heterologous nucleotide sequence, for expression in the plant of interest. By "heterologous nucleotide sequence" is intended to mean a sequence that is not naturally operably linked with the promoter sequence, including non-naturally occurring multiple copies of a naturally occurring DNA sequence. While this nucleotide sequence is heterologous to the promoter sequence, it may be homologous, or native, or heterologous, or foreign, to the plant host. It is recognized that the promoter may also drive expression of its homologous or native nucleotide sequence. In this case, the transformed plant will have a change in phenotype. Heterologous nucleotide sequences include, but are not limited to, insecticidal coding sequences, nematicidal coding sequences, herbicide-tolerance coding sequences, anti-microbial coding sequences, anti-fungal coding sequences, anti-viral coding sequences, abiotic stress tolerance coding sequences, nutritional quality coding sequences, visible marker coding sequences, and selectable marker coding sequences.

The expression of heterologous nucleotide sequences can vary depending upon the type of promoter utilized. One category of promoters known as "tissue-specific promoters" express the genes under their control in only one or more cell types in specific organs, specific tissues, or specific cell types. Tissue-specific promoters include promoters that are temporally regulated, such as in early or late embryogenesis, during fruit ripening in developing seeds or fruit, in fully differentiated leaf, or at the onset of senescence. In contrast, "constitutive promoters" refer to promoters that are able to express the genes under their control in all or nearly all of the plant tissues during all or nearly all developmental stages of the plant, thereby generating "constitutive expression" of the genes. Yet another type of promoter known as an "inducible promoter" is a type of regulated promoter that can be turned on in one or more cell types by an external stimulus, such as a chemical, light, hormone, stress, or a pathogen.

The regulatory sequences of the present invention, when operably linked to a heterologous nucleotide sequence of interest and stably incorporated into the plant genome drive "root-preferred" expression of the heterologous nucleotide sequence. By "root-preferred" is intended that expression of the heterologous nucleotide sequence is most abundant in the root. By "root" is intended to mean any part of the root structure, including but not limited to, the root cap, apical meristem, protoderm, ground meristem, procambium, endodermis, cortex, vascular cortex, epidermis, and the like. While some level of expression of the heterologous nucleotide sequence may occur in other plant tissue types, expression occurs most abundantly in the root, which may include, but is not limited to primary, lateral, and adventitious roots.

Modifications of the isolated promoter sequences of the present invention can provide for a range of expression of the heterologous nucleotide sequence. Thus, they may be modified to be weak promoters or strong promoters. Generally, by "weak promoter" is intended to mean a promoter that drives expression of a coding sequence of interest at a low level. By "low level" is intended to mean that the transcript for the coding sequence of interest represents about 1 out of every 10,000 transcripts to about 1 out of every 500,000 transcripts being produced in the cell at any given point in time. Conversely, under equivalent cellular conditions, a strong promoter drives expression of a coding sequence of interest at a high level, such that the transcript for the coding sequence of interest represents about 1 out of every 10 transcripts to about 1 out of every 1,000 transcripts being produced in the cell at any given point in time. Alternatively, it is recognized that weak promoters also encompass promoters that are expressed in only a few cells and not in others to give a total low level of expression at any given point in time.

Fragments and variants of the disclosed promoter sequences are also encompassed by the present invention. By "fragment" is intended to mean a portion of the promoter sequence. Fragments of a promoter sequence may retain biological activity and hence be capable of driving root-preferred expression of an operably linked nucleotide sequence. Thus, for example, less than the entire promoter sequence disclosed herein may be utilized to drive expression of an operably linked nucleotide sequence of interest, such as a nucleotide sequence encoding a heterologous protein. It is within the skill in the art to determine whether such fragments decrease expression levels or alter the nature of expression, i.e., constitutive or inducible expression. Alternatively, fragments of a promoter nucleotide sequence that are useful as hybridization probes, as described below, generally do not retain this regulatory activity. Thus, fragments of a promoter sequence may range from at least about 20 nucleotides, about 50 nucleotides, about 100 nucleotides, and up to the full-length promoter sequence of the invention.

Thus, a fragment of a CRWAQ81 promoter nucleotide sequence may encode a biologically active portion of the CRWAQ81 promoter or it may be a fragment that can be used as a hybridization probe or PCR primer using methods disclosed below. A biologically active portion of a CRWAQ81 promoter can be prepared by isolating a portion of one of the CRWAQ81 promoter nucleotide sequences of the invention and assessing the activity of that portion of the CRWAQ81 promoter. Nucleic acid molecules that are fragments of a promoter nucleotide sequence comprise at least 15, 20, 25, 30, 35, 40, 45, 50, 75, 100, 325, 350, 375, 400, 425, 450, 500, 550, 600, 650, 700, 800, 900, 950, 1000, 1050, 1100, 1150, 1200, 1500, 1800, 2000 contiguous nucleotides, or up to the number of nucleotides present in full-length promoter nucleotide sequence disclosed herein, e.g., 2136 nucleotides for SEQ ID NO:1. "Contiguous" nucleotides, as used herein, refers to nucleic acid sequences that are immediately preceding or following one another.

Nucleic acid molecules that are fragments of the full length CRWAQ81 promoter that are capable of functioning as a promoter may comprise, for example, nucleotides 931 to 2113 of SEQ ID NO:1; nucleotides 936 to 2113 of SEQ ID NO:1; nucleotides 941 to 2113 of SEQ ID NO:1; nucleotides 946 to 2113 of SEQ ID NO:1, nucleotides 951 to 2113 of SEQ ID NO:1; nucleotides 956 to 2113 of SEQ ID NO:1; nucleotides 961 to 2113 of SEQ ID NO:1; nucleotides 971 to 2113 of SEQ ID NO:1; nucleotides 981 to 2113 of SEQ ID NO:1; nucleotides 991 to 2113 of SEQ ID NO:1; nucleotides 1001 to 2113 of SEQ ID NO:1; nucleotides 1051 to 2113 of SEQ ID NO:1; nucleotides 1101 to 2113 of SEQ ID NO:1; nucleotides 1151 to 2113 of SEQ ID NO:1; nucleotides 1201 to 2113 of SEQ ID NO:1; nucleotides 1251 to 2113 of SEQ ID NO:1; nucleotides 1301 to 2113 of SEQ ID NO:1; nucleotides 1351 to 2113 of SEQ ID NO:1; nucleotides 1401 to 2113 of SEQ ID NO:1; nucleotides 1451 to 2113 of SEQ ID NO:1; nucleotides 1501 to 2113 of SEQ ID NO:1; nucleotides 1551 to 2113 of SEQ ID NO:1; nucleotides 1601 to 2113 of SEQ ID NO:1; nucleotides 1651 to 2113 of SEQ ID NO:1; nucleotides 1701 to 2113 of SEQ ID NO:1; nucleotides 1751 to 2113 of SEQ ID NO:1; nucleotides 1777 to 2113 of SEQ ID NO:1; nucleotides 1782 to 2113 of SEQ ID NO:1; nucleotides 1787 to 2113 of SEQ ID NO:1; nucleotides 1792 to 2113 of SEQ ID NO:1; nucleotides 1801 to 2113 of SEQ ID NO:1; nucleotides 1851 to 2113 of SEQ ID NO:1; nucleotides 1901 to 2113 of SEQ ID NO:1; nucleotides 1951 to 2113 of SEQ ID NO:1; nucleotides 931 to 2110 of SEQ ID NO:1; nucleotides 931 to 2107 of SEQ ID NO:1; nucleotides 931 to 2104 of SEQ ID NO:1; nucleotides 931 to 2100 of SEQ ID NO:1.

The nucleotides of such fragments will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol.* 155:335-350, and Erlich, ed. (1989) *PCR Technology* (Stockton Press, New York). Variants of these promoter fragments, such as those resulting from site-directed mutagenesis, are also encompassed by the compositions of the present invention.

By "variants" is intended to mean sequences having substantial similarity with a promoter sequence disclosed herein. For nucleotide sequences, a variant comprises a deletion and/or addition of one or more nucleotides at one or more internal sites within the native nucleic acid molecule and/or a substitution of one or more nucleotides at one or more sites in the native nucleic acid molecule. As used herein, a "native" nucleic acid molecule comprises a naturally occurring nucleotide sequence. Naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular nucleotide sequence as determined by sequence alignment programs and parameters described elsewhere herein.

Biologically active variants are also encompassed by the present invention. Biologically active variants include, for example, the native promoter sequence of the invention having one or more nucleotide substitutions, deletions, or insertions. Promoter activity may be measured by using techniques such as Northern blot analysis, reporter activity measurements taken from transcriptional fusions, and the like. See, for example, Sambrook et al. (1989) *Molecular Cloning: A Laboratory Manual* (2d ed., Cold Spring Harbor Laboratory Press, Cold Spring Harbor, N.Y.), herein incorporated by reference. Alternatively, levels of a reporter gene such as green fluorescent protein (GFP) or the like produced under the control of a promoter fragment or variant can be measured. See, for example, U.S. Pat. No. 6,072,050, herein incorporated by reference.

Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire CRWAQ81 promoter sequence set forth herein or to fragments thereof are encompassed by the present invention. Thus, isolated nucleic acid molecules that have promoter activity and which hybridize under stringent conditions to the promoter sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the CRWAQ81 promoter sequences of the invention. Methods for the preparation of probes for hybridization and for the construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire CRWAQ81 promoter sequences disclosed herein, or one or more portions thereof, may be used as a probe capable of specifically hybridizing to corresponding CRWAQ81 promoter sequences. To achieve specific hybridization under a variety of conditions, such probes include sequences that are unique among CRWAQ81 promoter sequences and are optimally at least about 10 nucleotides in length, and most optimally at least about 20 nucleotides in length. Such probes may be used to amplify corresponding CRWAQ81 promoter sequences from a chosen plant by PCR. This technique may also be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" conditions under which a probe will hybridize to its target sequence to a detectably greater degree than to other sequences (e.g., at least 2-fold over background) are intended. Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least 20 minutes. Duration of hybridization is generally less than about 24 hours, usually about 4 to about 12 hours. The duration of the wash time will be at least a length of time sufficient to reach equilibrium. Optionally, wash buffers may comprise about 0.1% to about 1% SDS.

Specificity is typically the function of post-hybridization washes, the critical factors being the ionic strength and temperature of the final wash solution. The $T_m$ (thermal melting point) is the temperature (under defined ionic strength and pH) at which 50% of a complementary target sequence hybridizes to a perfectly matched probe. For DNA-DNA hybrids, the $T_m$ can be approximated from the equation of Meinkoth and Wahl (1984) *Anal. Biochem.* 138:267-284: $T_m=81.5°$ C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See also Sambrook et al. (1989) *Molecular Cloning: A Laboratory Manual* (2d ed., Cold Spring Harbor Laboratory Press, Plainview, N.Y.).

Thus, isolated sequences that have root-preferred promoter activity and which hybridize under stringent conditions to the CRWAQ81 promoter sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", and (d) "percentage of sequence identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; and the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (Version 3.0, copyright 1997); and GAP, BESTFIT, BLAST, FASTA, and TFASTA in the Wisconsin Genetics Software Package of Genetics Computer Group, Version 10 (available from Accelrys, 9685 Scranton Road, San Diego, Calif., 92121, USA). The scoring matrix used in Version 10 of the Wisconsin Genetics Software Package is BLOSUM62 (see Henikoff and Henikoff (1989) *Proc. Natl. Acad. Sci. USA* 89:10915).

Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN and the ALIGN PLUS programs are based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the web site for the National Center for Biotechnology Information on the world wide web. Alignment may also be performed manually by inspection.

Unless otherwise stated, nucleotide sequence identity/similarity values provided herein refer to the value obtained using GAP Version 10 using the following parameters: % identity and % similarity for a nucleotide sequence using GAP Weight of 50 and Length Weight of 3; and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended to mean any sequence comparison program that, for any two sequences in question, generates an alignment having identical nucleotide or amino acid residue matches and an identical percent sequence identity when compared to the corresponding alignment generated by GAP Version 10.

The GAP program uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can each be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The CRWAQ81 promoter sequences disclosed herein are useful for genetic engineering of plants, e.g. for the production of a transformed or transgenic plant, to express a phenotype of interest. Various changes in phenotype are of interest including, but not limited to, modifying expression of a gene in a plant root, altering a plant's pathogen or insect defense mechanism, increasing the plant's tolerance to herbicides, altering root development to respond to environmental stress, and the like. These results can be achieved by providing expression of heterologous or increased expression of endogenous products in plants. Alternatively, the results can be achieved by providing for a reduction of expression of one or more endogenous products, particularly enzymes, transporters, or cofactors, or affecting nutrient uptake in the plant. These changes result in a change in phenotype of the transformed plant.

As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant expression cassette. It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct, including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that includes the heterologous DNA.

As used herein, the term "plant" includes reference to whole plants, plant organs (e.g., leaves, stems, roots, etc.), seeds, plant cells, and progeny of same. Parts of transgenic plants within the scope of the invention are to be understood to comprise, for example, plant cells, protoplasts, tissues, callus, embryos as well as flowers, stems, fruits, ovules, leaves, or roots originating in transgenic plants or their progeny previously transformed with a DNA molecule of the invention, and therefore consisting at least in part of transgenic cells.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest for the present invention include, but are not limited to, for example, those genes involved in information, such as Zinc fingers, those involved in communication, such as kinases, and those involved in housekeeping, such as heat shock proteins. More specific categories of transgenes, for example, include, but are not limited to, genes encoding proteins conferring resistance to abiotic stress, such as drought, temperature, salinity, and toxins such as pesticides and herbicides, or to biotic stress, such as attacks by fungi, viruses, bacteria, insects, and nematodes, and development of diseases associated with these organisms. It is recognized that any gene of interest can be operably linked to the promoter sequences of the invention and expressed in plant roots.

A DNA construct comprising one of these genes of interest can be used with transformation techniques, such as those described below, to create disease or insect resistance in susceptible plant phenotypes or to enhance disease or insect resistance in resistant plant phenotypes. Accordingly, the invention encompasses methods that are directed to protecting plants against fungal pathogens, bacteria, viruses, nematodes, insects, and the like. By "disease resistance" or "insect resistance" is intended to mean that the plants avoid the harmful symptoms that are the outcome of the plant-pathogen interactions.

Disease resistance and insect resistance genes such as lysozymes, cecropins, maganins, or thionins for antibacterial protection, or the pathogenesis-related (PR) proteins such as glucanases and chitinases for anti-fungal protection, or *Bacillus thuringiensis* endotoxins, protease inhibitors, collagenases, lectins, and glycosidases for controlling nematodes or insects are all examples of useful gene products.

Pathogens of the invention include, but are not limited to, viruses or viroids, bacteria, insects, nematodes, fungi, and the like. Viruses include but are not limited to tobacco or cucumber mosaic virus, ringspot virus, necrosis virus, maize dwarf mosaic virus, etc. Nematodes include but are not limited to parasitic nematodes such as root knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include but are not limited to *Pratylenchus* spp.

Genes encoding disease resistance traits include but are not limited to detoxification genes, such as against fumonisin (U.S. Pat. No. 5,792,931); avirulence (avr) and disease resistance (R) genes (Jones et al. (1994) *Science* 266:789; Martin et al. (1993) *Science* 262:1432; Mindrinos et al. (1994) *Cell* 78:1089); and the like.

Herbicide resistance traits may be introduced into plants by genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit the action of glutamine synthase, such as phosphinothricin or basta (e.g., the bar gene), glyphosate (e.g., the EPSPS gene and the GAT gene; see, for example, U.S. Publication No. 20040082770 and International Publication No. WO 03/092360) or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Exogenous products include plant enzymes and products as well as those from other sources including prokaryotes and other eukaryotes. Such products include enzymes, cofactors, hormones, and the like.

Examples of other applicable genes and their associated phenotype include but are not limited to the gene that encodes viral coat protein and/or RNA, or other viral or plant genes that confer viral resistance; genes that confer fungal resistance; genes that confer insect resistance; genes that promote yield improvement; and genes that provide for resistance to stress, such as dehydration resulting from heat and salinity, toxic metal or trace elements, or the like.

In other embodiments of the present invention, the CRWAQ81 promoter sequences are operably linked to genes of interest that improve plant growth or increase crop yields under high plant density conditions. For example, the CRWAQ81 promoter of the invention may be operably linked to nucleotide sequences expressing agronomically important genes that result in improved primary or lateral root systems. Such genes include, but are not limited to, nutrient/water transporters and growth inducers. Examples of such genes, include but are not limited to, maize plasma membrane $H^+$-ATPase (MHA2) (Frias et al. (1996) *Plant Cell* 8:1533-44); AKT1, a component of the potassium uptake apparatus in *Arabidopsis* (Spalding et al. (1999) *J. Gen. Physiol.* 113:909-18); RML genes, which activate cell division cycle in the root apical cells (Cheng et al. (1995) *Plant Physiol.* 108:881); maize glutamine synthetase genes (Sukanya et al. (1994) *Plant Mol. Biol.* 26:1935-46); and hemoglobin (Duff et al. (1997) *J. Biol. Chem.* 27:16749-16752; Arredondo-Peter et al. (1997) *Plant Physiol.* 115:1259-1266; Arredondo-Peter et al. (1997) *Plant Physiol.* 114:493-500 and the references cited therein). The CRWAQ81 promoter sequences may also be useful in expressing antisense nucleotide sequences of genes that negatively affect root development under high-planting density conditions.

The heterologous nucleotide sequence operably linked to the CRWAQ81 promoter and related promoter sequences disclosed herein may be an antisense sequence for a targeted gene. By "antisense DNA nucleotide sequence" is intended to mean a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having 70%, 80%, 85%, 90% or 95% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in the plant root.

In one embodiment of the invention, expression cassettes will comprise a transcriptional initiation region comprising one of the promoter nucleotide sequences disclosed herein, or variants or fragments thereof, operably linked to a heterologous nucleotide sequence whose expression is to be controlled by the root-preferred promoters of the invention. Such an expression cassette is provided with a plurality of restriction sites for insertion of the nucleotide sequence to be under the transcriptional regulation of the regulatory regions. The expression cassette may additionally contain selectable marker genes.

The expression cassette will include in the 5'-to-3' direction of transcription, a transcriptional and translational initiation region (i.e., a root-preferred promoter described herein), a heterologous nucleotide sequence of interest, and a transcriptional and translational termination region (i.e., termination region) functional in plants. The termination region may be native with the transcriptional initiation region comprising the promoter nucleotide sequence of the present invention, may be native with the DNA sequence of interest, may be native with the plant host, or may be derived from another source (i.e., foreign or heterologous to the promoter, the heterologous sequence of interest, the plant host, or any combination thereof). Convenient termination regions are available from the Ti-plasmid of *A. tumefaciens*, such as the octopine synthase and nopaline synthase termination regions. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; and Joshi et al. (1987) *Nucleic Acid Res.* 15:9627-9639.

The expression cassette comprising a promoter sequence of the present invention operably linked to a heterologous nucleotide sequence may also contain at least one additional nucleotide sequence for a gene to be cotransformed into the organism. Alternatively, the additional sequence(s) can be provided on another expression cassette.

The expression cassettes comprising a promoter sequence of the present invention may additionally contain 5' non-translated leader sequences or 5' non-coding sequences. As used herein, "5' leader sequence," "translation leader sequence," or "5' non-coding sequence" refer to that DNA sequence portion of a gene between the promoter and coding sequence that is transcribed into RNA and is present in the fully processed mMRNA upstream (5') of the translation start codon. A 5' non-translated leader sequence is usually characterized as that portion of the mRNA molecule which most typically extends from the 5' CAP site to the AUG protein translation initiation codon. The translation leader sequence may affect processing of the primary transcript to mRNA, mRNA stability or translation efficiency (Turner et al. (1995) *Molecular Biotechnology* 3:225). Thus, translation leader sequences play an important role in the regulation of gene expression. Translation leaders are known in the art and include but are not limited to: picornavirus leaders, for example, EMCV leader (Encephalomyocarditis 5' noncoding region) (Elroy-Stein et al. (1989) *Proc. Nat. Acad. Sci. USA* 86:6126-6130); potyvirus leaders, for example, TEV leader (Tobacco Etch Virus) (Allison et al. (1986)); MDMV leader (Maize Dwarf Mosaic Virus); human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) *Molecular Biology of RNA*, pages 237-256); and maize chlorotic mottle virus leader (MCMV) (Lommel et al. (1991) *Virology* 81:382-385). See also Della-Cioppa et al. (1987) *Plant Physiology* 84:965-968.

Various intron sequences have been shown to enhance expression, particularly in monocotyledonous cells. The introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., (1987) *Genes Develop.* 1:1183-1200). In the same experimental system, the intron from the maize bronze gene had a similar effect in enhancing expression. The AdhI intron has also been shown to enhance CAT expression 12-fold (Mascarenhas et al. (1990) *Plant Mol. Biol.* 6:913-920). Intron sequences have routinely been incorporated into plant transformation vectors, typically within the non-translated leader. See also, Christensen and Quail (1996) *Transgenic Res.* 5:213-218; Christensen et al. (1992) *Plant*

*Molecular Biology* 18:675-689; Kyozuka et al. (1991) *Mol. Gen. Genet.* 228:40-48; and Kyozuka et al. (1990) *Maydica* 35:353-357.

The expression cassette comprising a promoter sequence of the present invention may additionally contain a 3' non-coding sequence. A "3' non-coding sequence" or "3' non-translated region" refers to a nucleotide sequence located 3' (downstream) to a coding sequence and includes polyadenylation signal sequences and other sequences encoding regulatory signals capable of affecting the addition of polyadenylic acid tracts to the 3' end of the mRNA precursor. A 3' non-translated region comprises a region of the mRNA generally beginning with the translation termination codon and extending at least beyond the polyadenylation site. Non-translated sequences located in the 3' end of a gene have been found to influence gene expression levels. Ingelbrecht et al. (see, *Plant Cell,* 1:671-680, 1989) evaluated the importance of these elements and found large differences in expression in stable plants depending on the source of the 3' non-translated region. Using 3' non-translated regions associated with octopine synthase, 2S seed protein from *Arabidopsis*, small subunit of rbcS from *Arabidopsis*, extension from carrot, and chalcone synthase from Antirrhinium, a 60-fold difference was observed between the best-expressing construct (which contained the rbcS 3' non-translated region) and the lowest-expressing construct (which contained the chalcone synthase 3' region).

Transcription levels may also be increased by the utilization of enhancers in combination with the promoter regions of the invention. Enhancers are nucleotide sequences that act to increase the expression of a promoter region. Enhancers are known in the art and include the SV40 enhancer region, the 35S enhancer element, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites. Restriction sites may be added or removed, superfluous DNA may be removed, or other modifications may be made to the sequences of the invention. For this purpose, in vitro mutagenesis, primer repair, restriction, annealing, resubstitutions, for example, transitions and transversions, may be involved.

Reporter genes or selectable marker genes may be included in the expression cassettes. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213 and Meijer et al. (1991) *Plant Mol. Biol.* 16:807-820); hygromycin (Waldron et al. (1985) *Plant Mol. Biol.* 5:103-108 and Zhijian et al. (1995) *Plant Science* 108:219-227); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481 and U.S. patent application Ser. No. 10/004,357); and phosphinothricin (De-Block et al. (1987) *EMBO J.* 6:2513-2518).

Other genes that could serve utility in the recovery of transgenic events but might not be required in the final product would include, but are not limited to, examples such as GUS (b-glucoronidase; Jefferson (1987) *Plant Mol. Biol. Rep.* 5:387), GFP (green florescence protein; Chalfie et al. (1994) *Science* 263:802), luciferase (Riggs et al. (1987) *Nucleic Acids Res.* 15(19):8115 and Luehrsen et al. (1992) *Methods Enzymol.* 216:397-414), and the maize genes encoding for anthocyanin production (Ludwig et al. (1990) *Science* 247:449).

The nucleic acid molecules of the present invention are useful in methods directed to expressing a nucleotide sequence in a plant. This may be accomplished by transforming a plant cell of interest with an expression cassette comprising a promoter identified herein, operably linked to a heterologous nucleotide sequence, and regenerating a stably transformed plant from said plant cell. The methods of the invention are also directed to selectively expressing a nucleotide sequence in a plant root. Those methods comprise transforming a plant cell with an expression cassette comprising a promoter identified herein that initiates root-preferred transcription in a plant cell, operably linked to a heterologous nucleotide sequence, and regenerating a transformed plant from said plant cell.

The expression cassette comprising the particular promoter sequence of the present invention operably linked to a nucleotide sequence of interest can be used to transform any plant. In this manner, genetically modified, i.e. transgenic or transformed, plants, plant cells, plant tissue, seed, root, and the like can be obtained.

The present invention may be used for transformation of any plant species, including, but not limited to, monocots and dicots. Examples of plants of interest include, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus Cucumis such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Optimally, plants of the present invention are crop plants (for example, corn, alfalfa, sunflower, *Brassica*, soybean, cotton, safflower, peanut, sorghum, wheat, millet, tobacco, etc.), more optimally corn and soybean plants, yet more optimally corn plants.

This invention is particularly suitable for any member of the monocot plant family including, but not limited to, maize, rice, barley, oats, wheat, sorghum, rye, sugarcane, pineapple, yams, onion, banana, coconut, and dates.

As used herein, "vector" refers to a DNA molecule such as a plasmid, cosmid, or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, ampicillin resistance, or glyphosate resistance.

The methods of the invention involve introducing a nucleotide construct into a plant. By "introducing" is intended to mean to present to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "transient transformation" is intended to mean that a nucleotide construct introduced into a plant does not integrate into the genome of the plant. By "stable transformation" is intended to mean that the nucleotide construct introduced into a plant integrates into the genome of the plant and is capable of being inherited by progeny thereof. By "primary transformant" and "T0 generation" transgenic plants that are of the same genetic generation as the tissue that was initially transformed (i.e., not having gone through meiosis and fertilization since transformation) are intended. "Secondary transformants" and the "T1, T2, T3, and subsequent generations" refer to transgenic plants derived from primary transformants through one or more meiotic and fertilization cycles. They may be derived by self-fertilization of primary or secondary transformants or crosses of primary or secondary transformants with other transformed or untransformed plants.

The nucleotide constructs of the invention may be introduced into plants by contacting plants with a virus or viral nucleic acids. Generally, such methods involve incorporating a nucleotide construct of the invention within a viral DNA or RNA molecule. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367, and 5,316,931; herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,981,840 and 5,563,055), direct gene transfer (Paszkowski et al. (1984) *EMBO J.* 3:2717-2722), and ballistic particle acceleration (see, for example U.S. Pat. Nos. 4,945,050; 5,879,918; 5,886,244; and 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926) and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the heterologous sequence of interest can be provided to a plant using a variety of transient transformation methods. Such transient transformation methods include, but are not limited to, the introduction of the heterologous protein or variants and fragments thereof directly into the plant or the introduction of the a heterologous transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the heterologous polynucleotide of interest can be transiently transformed into the plant using techniques known in the art. Such techniques include viral vector system and the precipitation of the polynucleotide in a manner that precludes subsequent release of the DNA. Thus, the transcription from the particlebound DNA can occur, but the frequency with which its released to become integrated into the genome is greatly reduced. Such methods include the use particles coated with polyethylimine (PEI; Sigma #P3143).

Methods are known in the art for the targeted insertion of a polynucleotide at a specific location in the plant genome. In one embodiment, the insertion of the polynucleotide of interest at a desired genomic location is achieved using a site-specific recombination system. See, for example, WO99/25821, WO99/25854, WO99/25840, WO99/25855, and WO99/25853, all of which are herein incorporated by reference. Briefly, the heterologous polynucleotide of interest can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having root-preferred expression of the desired phenotypic characteristic identified. Two or more generations may be grown to ensure that root-preferred expression of the desired phenotypic characteristic is stably maintained and inherited and then seeds harvested to ensure root-preferred expression of the desired phenotypic characteristic has been achieved. Thus as used herein, "transformed seeds" refers to seeds that contain the nucleotide construct stably integrated into the plant genome.

Several methods are available to assess promoter activity using both transient and stable transformation methods. Expression cassettes may be constructed with a marker such as a visible marker. Using transformation methods such as microprojectile bombardment, *Agrobacterium* transformation or protoplast transformation, expression cassettes are delivered to plant cells or tissues. Reporter gene activity, such as β-glucuronidase activity, luciferase activity or GFP fluorescence is monitored over time after transformation, for example 2 hours, 5 hours, 8 hours, 16 hours, 24 hours, 36 hours, 48 hours and 72 hours after DNA delivery using methods well known in the art. Reporter gene activity may be monitored by enzymatic activity, by staining cells or tissue with substrate for the enzyme encoded by the reporter gene or by direct visualization under an appropriate wavelength of light. Full-length promoter sequences, deletions and mutations of the promoter sequence may be assayed and their expression levels compared. Additionally, RNA levels may be measured using methods well known in the art, such as, Northern blotting, competitive reverse transcriptase PCR and RNAse protection assays. These assays measure the level of expression of a promoter by measuring the "steady state" concentration of a standard transcribed reporter mRNA. This measurement is indirect since the concentration of the reporter mRNA is dependent not only on its synthesis rate, but also on the rate with which the mRNA is degraded. Therefore the steady state level is the product of synthesis rates and degradation rates. The rate of degradation can however be considered to proceed at a fixed rate when the transcribed sequences are identical, and thus this value can serve as a measure of synthesis rates.

Further confirmation of promoter activity is obtained by stable transformation of the promoter in an expression cassette comprising a visible marker or gene of interest into a plant as described above. Using the various methods described above such as enzymatic activity assays, RNA analysis and protein assays, promoter activity may be monitored over development, and additionally monitored in different tissues in the primary transformants and through subsequent generations of transgenic plants.

The invention provides compositions for screening compounds that modulate expression within roots of embryos and plants, and within root nodules. The vectors, cells, and plants can be used for screening candidate molecules for agonists and antagonists of the CRWAQ81 promoter. For example, a reporter gene can be operably linked to a CRWAQ81 promoter and expressed as a transgene in a plant. Compounds to be tested are added and reporter gene expression is measured to determine the effect on promoter activity.

The following examples are offered by way of illustration and not by way of limitation.

EXAMPLES

Example 1

Identification of the EST, CRWAQ81

The expressed sequence tag (EST) named CRWAQ81 was first identified using a proprietary sequence analysis program. This program contained an algorithm that allowed ESTs from all proprietary root-related maize libraries to be compared to ESTs from all proprietary non-root maize libraries. ESTs, or groupings of overlapping ESTs referred to as contigs, which were returned by the program, were identified as root preferred or potentially root specific.

The EST named CRWAQ81 was identified in a root-preferred contig comprised of 13 unique ESTs, 11 of which were from root libraries. Eight of those 11 were from a root library synthesized from 2-3 day old germinating seedlings and the remaining 3 were from a root library generated from western corn rootworm (WCRW) infested V5-stage plants (V5-stage plants have 5 collared leaves). The 2 non-root ESTs were from shoot libraries made from 2-3 day old seedlings. The EST CRWAQ81 was selected for further characterization because it comprised all but approximately 78 bp of the 703 bp contig.

Further evidence that the CRWAQ81 EST is root-preferred was obtained using Massively Parallel Signature Sequencing technology (MPSS) (see, Brenner, et al. (2000) *Nature Biotechnology* 18:630-634 and Brenner et al. (2000) *Proc. Natl. Acad. Sci. USA* 97:1665-1670). This technology involves the generation of 17 base signature tags from mRNA samples that have been reverse transcribed. The tags are simultaneously sequenced and assigned to genes or ESTs. The abundance of these tags is given a numeric value that is normalized to parts per million (PPM) which then allows the tag expression, or tag abundance, to be compared across different tissues. Thus, the MPSS platform can be used to determine the expression pattern of a particular gene and its expression level in different tissues.

The sequence of the CRWAQ81 EST was entered into the MPSS database and the signature tag was identified starting approximately 247 bases upstream of the poly(A) site. The tag was found to be in root libraries at levels averaging an adjusted PPM of 2126. This level is comparable to the maize ubiquitin gene, which had an adjusted PPM value of 2916. The maize ubiquitin gene is considered to be a highly expressed gene and therefore was used as a reference to compare expression levels. These results also indicated that the CRWAQ81 EST is root-preferred. The tag for CRWAQ81 was found in 2 non-root libraries in the MPSS database, specifically an endosperm library at an adjusted PPM of 3, and a leaf library at an adjusted PPM of 5. These PPM values indicated the level of expression in these tissues was essentially at background. These data indicated that the gene for CRWAQ81 is root-preferred and expressed at relatively high levels.

Example 2

CRWAQ81 is Not Down-Regulated by WCRW Feeding

An important feature of a promoter directing expression of an insecticidal gene is that it is not down-regulated by insect feeding. For the CRWAQ81 gene, down regulation in response to WCRW feeding was tested. For testing, fluorescently labeled cRNA was generated from leaves, stems, nodal roots, and lateral roots of V6-stage plants (V6 stage plants have 6 collared leaves) and hybridized to an Affymetrix® DNA microarray chip containing oligonucleotide probes of the CRWAQ81 EST.

Results indicated that, in uninfested plants, CRWAQ81 was expressed at levels 240-fold higher in lateral roots than in leaves. The gene was also expressed at levels 240-fold greater in lateral roots than in stems. These results indicated that the CRWAQ81 gene is expressed at high levels in root tissues, but not in leaf or stem tissue. Comparing lateral roots to nodal roots showed a less than two-fold difference in CRWAQ81 gene expression. Thus, between the two root types, there is virtually no difference in the CRWAQ81 gene expression level.

When tissues were compared between WCRW infested and uninfested plants, virtually no differences in CRWAQ81 expression levels were found. In particular, a less than two-fold difference in expression was detected between the roots of WCRW-infested plants and the roots of uninfested plants. These results were supported by the MPSS platform, which showed there was only a 25% difference in CRWAQ81 expression levels between the roots of WCRW infested plants and uninfested plants. Thus, these data indicate that the gene for CRWAQ81 is not significantly down regulated by WCRW feeding and remains at a high expression level.

Materials and Methods

Maize plants from the B73 line were grown under greenhouse conditions to V6-stage (6 collared leaves). Leaves (V6 leaf), stem (stalk), elongating nodal roots, and adventitious lateral roots were harvested from WCRW infested and uninfested plants. For the WCRW infested plants, WCRW eggs were applied at a rate of 50 per plant. This level of infestation produced roots that were damaged and scarred, but not decimated.

RNA was extracted from approximately 200 mg of tissue using Trizol® reagent (Invitrogen, Carlsbad, Calif.). PolyA+ RNA(~1.0 µg) was isolated using PolyATtract® mRNA Isolation System IV (Promega, Madison, Wis.). Double-stranded cDNA was synthesized using the SuperScript™ II Plasmid System (Invitrogen). In vitro transcription labeling of cRNA with biotin conjugated ribonucleotides was performed with the MEGAscript® T7 kit (Ambion, Inc., Austin, Tex.) followed by the QIAGEN, Inc. (Valencia, Calif.) RNeasy® mini protocol for RNA cleanup. The resulting cRNA was fragmented and hybridized for 16 hours to a customized GeneChip® array of Zea mays oligonucleotides, then washed and stained with streptavidin, R-phycoerythrin conjugate, using the Affymetrix® GeneChip Fluidics Station. The Hewlett-Packard G2500A Gene Array Scanner and Affymetrix® GeneChip Analysis Suite software were used to analyze the results.

Example 3

Northern Analysis of CRWAQ81 Expression

Northern blot analysis was performed to further demonstrate the spatial expression preference for the CRWAQ81 gene. RNA derived from leaves and whole ears of R1 stage B73 maize plants (the R1 stage is identified by pollen-shed/silking) were electrophoresed and blotted with RNA from leaves, stem, lateral and nodal roots of WCRW-infested and uninfested V6 stage B73 maize plants. The blot was hybridized with probes synthesized from the CRWAQ81 EST.

No hybridization was observed in lanes containing leaf RNA from R1 stage or WCRW-infested and uninfested V6 stage plants. Similarly, no hybridization was observed in lanes containing RNA from R1 stage ears or V6 stage stems. Strong hybridization was only detected in lanes containing RNA from root tissue. This was independent of whether the roots were sampled from WCRW-infested or uninfested plants. These results provide further evidence that the CRWAQ81 gene is expressed at a high level, is root-preferred and is not down regulated by WCRW feeding.

Materials and Methods

Maize plants from the line, B73, were grown under greenhouse conditions to the R1 stage (pollen shed/silking). Leaves (leaf #11), whole ears (including husk, silk, and shank), and whole tassels (including anthers/pollen) were harvested. B73 plants were also grown to the V6 stage, infested with WCRW, and sampled as described in Example 2. Uninfested V6 stage plants were also sampled, as described in Example 2. RNA was extracted from the different tissues using Trizol® reagent (Invitrogen, Carlsbad, Calif.). The RNA samples were electrophoresed through a standard formaldehyde gel. Afterwards, the gel was washed 2 times in 20×SSC for a total of 15 minutes, then blotted to a nylon membrane overnight in 10×SSC. The membrane was UV-crosslinked for 2 minutes. Pre-hybridization of the blot totaled 2 hrs at 42° C. in 5×SSC, 2% Blocking reagent for nucleic acid hybridization, 0.1% N-laurylsarcosine, 7% SDS, 50% Formamide (UL-TRAhyb®, Ambion, Austin, Tex.). Single-stranded DNA probes were made from the CRWAQ81 EST by PCR. 50 ng of denatured probe was added per 1 ml of ULTRAhyb® solution. Hybridization was allowed to go overnight at 42° C. in 10 ml of solution. The next day the membrane was washed twice in 2× wash solution (2×SSC containing 0.1% SDS) at room temperature for 15 minutes, and then washed twice in 0.5× wash solution (0.5×SSC containing 0.1% SDS) at 65° C. for 15 minutes.

Visualization of the CRWAQ81 transcripts was accomplished using the Genius System from Boehringer Mannheim. Briefly, the membrane was equilibrated in Buffer 1 (100 mM Maleic Acid, 150 mM NaCl, pH 7.5) for 1 minute, then put in blocking solution (1% Blocking reagent for nucleic acid hybridization in Buffer 1) for 1 hour. The membrane was incubated in anti-DIG-alkaline phosphate diluted 1:10,000 in blocking solution for 30 minutes and washed 2 times in Buffer 1 for a total of 15 minutes. After equilibration in Buffer 3 (100 mM Tris-HCl, 100 mM NaCl, pH 9.5) for 2 minutes, twenty drops of CSPD (Roche Applied Science, Indianapolis, Ind., catalog no. 1755633) were applied to the membrane. It was covered with a plastic page protector and exposed to X-ray film overnight.

Example 4

In situ Hybridization

In situ RNA hybridization experiments were performed according to the protocol set forth in Di Laurenzio et al. (1996) *Cell* 86:423-433, to determine the cell-specific expression pattern of the CRWAQ81 gene in maize root tips. The hybridization experiments were performed in duplicate using embedded primary roots of maize seedlings grown on germination paper. An antisense probe and a sense probe were generated from the EST clone, CRWAQ81, using a PCR-based approach.

Hybridization with antisense probes from the CRWAQ81 EST indicated that the gene is almost ubiquitously expressed in maize root tips. Signal was detected in the epidermis, cortex, endodermis, and stele (pericycle and vascular tissue). Signal was not detected in the root cap, including the columella. Sense probes from the CRWAQ81 EST produced a similar hybridization pattern. While the intensity of the signal was relatively high, the level was less than observed with the antisense probe.

Example 5

Isolation of the Promoter for the CRWAQ81 Gene

Analysis of the CRWAQ81 gene indicated it was expressed at high levels and in a root-preferred manner. Thus, the CRWAQ81 promoter could be used to direct high levels of expression in the roots of transgenic maize. A ~2.1 kb DNA fragment (SEQ ID NO: 1) and a ~3.6 kb DNA fragment (SEQ ID NO: 2) of 5' flanking sequence was isolated using a combination of TAIL PCR (Liu et al. (1995) *Plant J.* 8:457-463) and ligation-mediated PCR (Universal GenomeWalker kit, Clontech).

To define the putative 3' end of the promoter, 5' RACE (Invitrogen, Life Technologies) was performed, according to the manufacturer's protocol. Sequence analysis of the RACE products revealed a single transcription start site approximately 34 bp upstream of the putative CRWAQ81 coding region. This was corroborated by the position of a putative TATA signal (TATAAAAT) located at −25 bp relative to the transcription start site.

Further analysis of the 5' flanking sequence revealed 2 large imperfect tandem repeats. The repeat most proximal to the transcription start site, designated as Repeat A2, is located at −500 bp relative to the start site and is approximately 745 bp in length. The repeat distal to the start site, designated as Repeat A1, is located at −1368 bp and is approximately 738 bp in length.

Located in the CRWAQ81 promoter are sequences with significant similarity to miniature inverted-repeat transposable elements (MITEs). MITEs are short transposable elements ranging in size from 125-500 bp that have been found in the non-coding regions of maize genes, including promoters (Wessler et al. (1995) *Current Opinion in Genetics & Development* 5:814-821). While MITE biology continues to be studied, one present school of thought considers MITES to play important roles such as providing regulatory sequences, like a TATA box or a transcription start site, or the like. Interestingly, 2 of the MITEs in the CRWAQ81 promoter region share homology to MITEs found in 2 other maize promoters.

The MITE sequence most proximal to the CRWAQ81 coding region is located at −408, relative to the transcription start site. It has 77% nucleotide identity to a MITE sequence found in the *Zea mays* P-gene promoter (Derwent GeneSeq Accession No. AAV32438). The other 2 MITE sequences, designated MITE1 and MITE2, overlap each other. MITE1 is located at −975 and has 79% identity to a MITE sequence in intron 3 of the *Zea mays* GapC4 gene (GenBank Accession No: X73152). MITE2, located at −948, has 65% identity to a MITE sequence in the promoter of the maize 22 kd alpha zein gene (GenBank Accession No: X61085).

Example 6

Promoter Activity of CRWAQ81

To demonstrate that the DNA fragments isolated as the CRWAQ81 promoter function as a promoter, a series of transient assays were performed. These assays provided a rapid assessment of whether the DNA fragment tested is able to direct gene expression. The ~2.1 kb promoter fragment (SEQ ID NO: 1), a component of the ~3.6 kb promoter sequence (SEQ ID NO: 2), was introduced into an expression cassette housing the β-glucuronidase (GUS) gene. Biolistic bombardment of root tissue from 5-day-old maize seedlings with this expression cassette resulted in the appearance of blue foci upon histochemical GUS staining. This indicated that the CRWAQ81 promoter fragment was able to direct gene expression.

Promoter activity was further demonstrated in transient assays using immature embryos and *Agrobacterium*-mediated transformation according to the protocol set forth in U.S. Pat. No. 5,981,840. During the cocultivation process with *Agrobacterium*, transient expression can be detected, even from some tissue-preferred promoters, e.g. from root-preferred promoters. For the ~2.1 kb CRWAQ81 promoter fragment, immature embryos were stained for GUS activity after 2 days and 5 days cocultivation. At 2 days, no GUS staining was observed. However, at 5 days low levels of punctate GUS staining were observed on the outer edges of the scutellum surrounding the embryo. This confirmed promoter activity, as negative controls lacked staining at both time points.

Materials and Methods

B73 seeds were placed along one edge of growth paper soaked in a solution of 7% sucrose. An additional piece of growth paper identical in size to the first was also soaked in 7% sucrose and overlaid onto the seeds. The growth paper—seed—growth paper sandwich was subsequently jelly rolled with the seed edge at the top of the roll. The roll was directionally placed into a beaker of 7% sucrose solution with the seeds at the top to allow for straight root growth. Seeds were allowed to germinate and develop for 2-3 days in the dark at 27-28° C. Prior to bombardment the outer skin layer of the cotyledon was removed and seedlings were placed in a sterile petri dish (60 mm) on a layer of Whatman #1 filter paper moistened with 1 ml of $H_2O$. Two seedlings per plate were arranged in opposite orientations and anchored to the filter paper with a 0.5% agarose solution. 2-3 cm root tip sections were also excised from seedlings and arranged lengthwise in the plates for bombardment.

DNA/gold particle mixtures were prepared for bombardment in the following method. Sixty mg of 0.6-1.0 micron gold particles were pre-washed with ethanol, rinsed with sterile distilled $H_2O$, and resuspended in a total of 1 ml of sterile $H_2O$. 50 μl aliquots of gold particle suspension were stored in siliconized Eppendorf tubes at room temperature.

DNA was precipitated onto the surface of the gold particles by combining, in order, 50 μl aliquot of pre-washed 0.6 μM gold particles, 5-10 μg of test DNA, 50 μl 2.5 M CaCl$_2$ and 25 μl of 0.1 M spermidine. The solution was immediately vortexed for 3 minutes and centrifuged briefly to pellet the DNA/gold particles. The DNA/gold was washed once with 500 μl of 100% ethanol and suspended in a final volume of 50 μl of 100% ethanol. The DNA/gold solution was incubated at −20° C. for at least 60 minutes prior to aliquoting 6 μl of the DNA/gold mixture onto each mylar macrocarrier.

Seedlings prepared as indicated above and excised root tips were bombarded twice using the PDS-1000/He gun at 1100 psi under 27-28 inches of Hg vacuum. The distance between macrocarrier and stopping screen was between 6-8 cm. Plates were incubated in sealed containers for 24 h in the dark at 27-280° C. following bombardment.

After 18-24 h of incubation the bombarded seedlings and root tips were assayed for transient GUS expression. Seedlings and excised roots were immersed in 10-15 mls of assay buffer containing 100 mM NaH$_2$PO$_4$—H$_2$O (pH 7.0), 10 mM EDTA, 0.5 mM K$_4$Fe(CN)$_6$-3H$_2$O, 0.1% Triton X-100 and 2 mM 5-bromo-4-chloro-3-indoyl glucuronide. The tissues were incubated in the dark for 24 h at 37° C. Replacing the GUS staining solution with 100% ethanol stopped the assay. GUS expression/staining was visualized under a microscope.

Example 7

Expression Pattern of CRWAQ81

Stable transformed plants were created to allow for a more detailed characterization of promoter activity, including expression pattern, expression level, and temporal regulation of the promoter.

Calli stably transformed with expression cassettes containing the ~2.1 kb CRWAQ81 promoter fragment (SEQ ID NO:1) operably connected to the GUS gene (abbreviated as CRWAQ81:GUS) or the ~2.1 kb CRWAQ81 promoter fragment operably linked to the Adh1 intron and the GUS gene (abbreviated as CRWAQ81 (Adh1 intron1):GUS) were histochemically stained for GUS activity. The Adh1 intron was included for the purpose of increased expression as it has been shown that in cereal cells the expression of foreign genes is enhanced by the presence of an intron in gene constructs (See, Callis et al. (1987) *Genes and Development* 1: 1183-1200 and Kyozuka et al. (1990) *Maydica* 35:353-357). Results from histochemical staining revealed a small number of callus events expressing GUS. The presence of the Adh1 intron increased the number of expressing events by a factor of 3. Most of the staining was localized to the somatic embryos, however, some callus staining was observed. These results support the transient assay results and demonstrate that the CRWAQ81 promoter fragment directs gene expression in callus events.

Leaf and root tissue from regenerated plants growing on nutrient agar were histochemically assayed for GUS activity. A few CRWAQ81:GUS events stained for GUS and most events transformed with the CRWAQ81 (Adh1 intron1):GUS vector expressed GUS. This indicated that the ~2.1 kb CRWAQ81 promoter fragment was active. In both cases, however, expression tended to be low. The expression pattern directed by the ~2.1 kb CRWAQ81 promoter fragment in regenerated plants was primarily root-preferred. Much of the expression was in the mature regions of the root (>1 cm from the root tip) and spatially split between 2 types of expression: ubiquitous expression in all cell types and localized expression in the vascular cylinder. In the root tip (the first 1 cm), no expression was detected. Nor was expression detected in emerging lateral roots (<1 cm in length).

Factors such as developmental stage may affect expression from this promoter fragment. Evidence for this hypothesis stems from two observations. First, the ~2.1 kb CRWAQ81 promoter fragment appears to be more active in V5-stage (5 collared leaves) greenhouse plants. Of 10 CRWAQ81:GUS transformation events sent to the greenhouse for potting in soil, only 3 were GUS positive in tissue culture (i.e., growing on nutrient agar). When the same plants were assayed at the V5-stage in the greenhouse, 9 of the 10 were GUS positive. A similar phenomenon was observed in CRWAQ81 (Adh1 intron1):GUS events, but to a lesser extent as most of the plants initially sent to the greenhouse for potting in soil were already GUS positive. The increased expression is not likely a result of increased GUS accumulation caused by low turnover of the GUS protein because an experiment looking at a group of CRWAQ81:GUS and CRWAQ81 (Adh1 intron1):GUS plants at V5-stage, and then again at R1 stage showed no difference in staining level. In addition, an examination of the Lynx MPSS database showed an incremental increase in expression of the CRWAQ81 gene between V2- and R1-stage. Specifically, the adjusted PPM value at V2-stage was 944. At V6 stage, the adjusted PPM value was near 1772, and at R1-stage the adjusted PPM value was 2870. Thus, the increased expression in older plants may be a result of temporal regulation of the CRWAQ81 promoter fragment. The spatial pattern of expression remained root-preferred in V5-stage plants. For CRWAQ81:GUS events, expression was ubiquitous in the mature regions of the root. No expression was observed in root tips (the first 1 cm) or in the emerging lateral roots (<1 cm in length). Few events had staining in the leaves. The expression pattern in CRWAQ81(Adh1 intron1):GUS events, however, was noticeably different. Expression was ubiquitous in the mature regions of the root. Expression was also observed in the root cap and weakly in the region of elongation of some events. Approximately 50% of the events showed some level of expression in the leaf vasculature. The reason for the ectopic expression is unclear. Expression in the silks at R1-R2 stage was also examined (at R2 stage the silks are protruding from the end of the ear and are beginning to dry out and darken in color). None of the events assayed showed expression. This included events both with and without the Adh1 intron. No GUS expression was observed in pollen. Again, this was true whether the Adh1 intron was present or not. In the tassels, essentially no expression was observed in the glumes or rachis of CRWAQ81:GUS plants. Weak staining was observed in the glumes and rachis of a few CRWAQ81 (Adh1 intron1):GUS plants. However, the most significant difference between the CRWAQ81:GUS and CRWAQ81 (Adh1 intron1):GUS tassels was the observed staining in the tissues near the lodicules. In CRWAQ81 (Adh1 intron1):GUS plants, most of the events had some level of GUS staining. Without the intron, only a few events stained in this region.

Materials and Methods

Histochemical Staining of Calli and Plant Tissues for GUS Activity

GUS activity was evaluated in the root cap, the meristem, region of elongation, and mature regions of excised roots. Leaf sections excised from near the tip of the youngest collared leaf were also evaluated. Detection of GUS activity was accomplished by placing tissue from regenerated transformed plants into 48-well plates containing 0.5 ml GUS assay buffer (assay buffer recipe described in Example 6) or in the case of greenhouse-grown plants, a 12-well plate containing 2 ml GUS assay buffer. Plates were placed under house vacuum for 10 min, then incubated in the dark at 37° C. overnight. Tissue was cleared of pigmentation with 2 successive 12 hr incubations in 100% ethanol at room temperature. The tissues were stored in 70% ethanol at 4° C.

Staining of excised silks and tassel branches was similar to leaf and root tissue except that the tissues were placed in 6-well plates containing 3-5 mls of GUS assay buffer. The tissues were cleared of pigmentation, as described above. Histochemical GUS staining of calli was performed as described for immature embryos in Example 6.

Example 8

Transformation of Maize by Particle Bombardment and Regeneration of Transgenic Plants Immature maize embryos from greenhouse donor plants are bombarded with DNA molecules containing a promoter of the invention operably linked to a gene of interest. A selectable marker is provided in the same transformation vector, or alternatively, the selectable marker gene is provided on a separate DNA molecule. Transformation is performed as follows. Media recipes follow below.

Preparation of Target Tissue

The ears are husked and surface sterilized in 30% Clorox™ bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a promoter sequence of the invention is made. The vector additionally contains a PAT selectable marker gene driven by a CaMV35S promoter and includes a CaMV35S terminator. Optionally, the selectable marker can reside on a separate plasmid. A DNA molecule comprising a promoter sequence of the invention as well as a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to a tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression by assays known in the art, such as, for example, immunoassays and western blotting with an antibody that binds to the protein of interest.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with dI $H_2O$ following adjustment to pH 5.8 with KOH); 2.0 g/l Gelrite™ (added after bringing to volume with dI $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with dI $H_2O$ following adjustment to pH 5.8 with KOH); 3.0 g/l Gelrite™ (added after bringing to volume with dI $H_2O$); and 0.85 mg/l silver nitrate and 3.0 mg/l Bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCl, 0.10 g/l pyridoxine HCl, and 0.40 g/l Glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished dI $H_2O$ after adjusting to pH 5.6); 3.0 g/l Gelrite™ (added after bringing to volume with dI $H_2O$); and 1.0 mg/l indoleacetic acid and 3.0 mg/l Bialaphos (added after sterilizing the medium and cooling to 60° C.). Hormone-free medium (272 V) comprises 4.3 g/l MS salts (GIBCO 11117-074), 5.0 ml/l MS vitamins stock solution (0.100 g/l nicotinic acid, 0.02 g/l thiamine HCl, 0.10 g/l pyridoxine HCl, and 0.40 g/l Glycine brought to volume with polished dI $H_2O$), 0.1 g/l myo-inositol, and 40.0 g/l sucrose (brought to volume with polished dI $H_2O$ after adjusting pH to 5.6); and 6 g/l Bacto-agar (added after bringing to volume with polished dI $H_2O$), sterilized and cooled to 60° C.

Example 9

*Agrobacterium*-Mediated Transformation of Maize and Regeneration of Transgenic Plants For *Agrobacterium*-mediated transformation of maize with a promoter sequence of the invention, optimally the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium* under conditions whereby the bacteria are capable of transferring the promoter sequence of the invention to at least one cell of at least one of the immature embryos (step 1: the infection step). In this step the immature embryos are optimally immersed in an *Agrobacterium* suspension for the initiation of inoculation. The embryos are co-cultured for a time with the *Agrobacterium* (step 2: the co-cultivation step). Optimally the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Optimally the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Optimally, the immature embryos are cultured on solid medium with a selective agent resulting in the selective growth of transformed cells. The callus is then regenerated into plants (step 5: the regeneration step), and optimally calli grown on selective medium are cultured on solid medium to regenerate the plants.

All publications, patents and patent applications mentioned in the specification are indicative of the level of those skilled in the art to which this invention pertains. All publications, patents and patent applications are herein incorporated by reference to the same extent as if each individual publication, patent or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

That which is claimed:

1. An isolated nucleic acid molecule comprising a nucleotide sequence selected from the group consisting of:
   a) a nucleotide sequence comprising the sequence set forth in SEQ ID NO:1 or SEQ ID NO:2;
   b) a nucleotide sequence comprising a plant promoter sequence that comprises at least 800 contiguous nucleotides of the plasmids deposited as Patent Deposit No. PTA-5126; and
   c) a nucleotide sequence comprising at least 800 contiguous nucleotides of the sequence set forth in SEQ ID NO:1 or SEQ ID N0:2, wherein said sequence initiates transcription in a plant cell.

2. An expression cassette comprising a nucleotide sequence of claim 1 operably linked to a heterologous nucleotide sequence of interest.

3. A vector comprising the expression cassette of claim 2.

4. A plant cell having stably incorporated into its genome the expression cassette of claim 2.

5. The plant cell of claim 4, wherein said plant cell is from a monocot.

6. The plant cell of claim 5, wherein said monocot is maize.

7. The plant cell of claim 4, wherein said plant cell is from a dicot.

8. A plant having stably incorporated into its genome the expression cassette of claim 2.

9. The plant of claim 8, wherein said plant is a monocot.

10. The plant of claim 9, wherein said monocot is maize.

11. The plant of claim 8, wherein said plant is a dicot.

12. A transgenic seed of the plant of claim 8.

13. The plant of claim 8, wherein the heterologous nucleotide sequence of interest encodes a gene product that confers herbicide, salt, pathogen, drought, cold, or insect resistance.

14. An expression cassette comprising, in sequence, the nucleic acid molecule of claim 1 operably linked to a heterologous nucleotide sequence of interest, which is operably linked to a 3' non-translated region including a polyadenylation signal.

15. A vector comprising the expression cassette of claim 14.

16. A plant cell having stably incorporated into its genome the expression cassette of claim 14.

17. A plant having stably incorporated into its genome the expression cassette of claim 14.

18. A transgenic seed of the plant of claim 17.

19. The plant of claim 17, wherein the heterologous nucleotide sequence of interest encodes a gene product that confers herbicide, salt, pathogen, drought, cold, or insect resistance.

20. A method for expressing a nucleotide sequence in a plant, said method comprising introducing into a plant cell an expression cassette, said expression cassette comprising a promoter and operably linked to said promoter a heterologous nucleotide sequence of interest, wherein said promoter comprises a nucleotide sequence selected from the group consisting of:
   a) a nucleotide sequence comprising the sequence set forth in SEQ ID NO:1 or SEQ ID NO:2;
   b) a nucleotide sequence comprising a plant promoter sequence that comprises at least 800 contiguous nucleotides of the plasmids deposited as Patent Deposit No. PTA-5126; and
   c) a nucleotide sequence comprising at least 800 contiguous nucleotides of the sequence set forth in SEQ ID NO:1 or SEQ ID NO:2, wherein said sequence initiates transcription in a plant cell.

21. The method of claim 20, wherein said heterologous nucleotide sequence of interest is selectively expressed in roots.

22. The method of claim 20, wherein said plant is a dicot.

23. The method of claim 20, wherein said plant is a monocot.

24. The method of claim 20, wherein said monocot is maize.

25. The method of claim 20, wherein the heterologous nucleotide sequence of interest encodes a gene product that confers herbicide, salt, pathogen, drought, cold, or insect resistance.

26. A method for expressing a nucleotide sequence in a plant cell, said method comprising introducing into said plant cell an expression cassette comprising a promoter operably linked to a heterologous nucleotide sequence of interest, wherein said promoter comprises a nucleotide sequence selected from the group consisting of:
   a) a nucleotide sequence comprising the sequence set forth in SEQ ID NO:1 or SEQ ID NO:2;
   b) a nucleotide sequence comprising a plant promoter sequence that comprises at least 800 contiguous nucleotides of the plasmids deposited as Patent Deposit No. PTA-5126; and
   c) a nucleotide sequence comprising at least 800 contiguous nucleotides of the sequence set forth in SEQ ID NO:1 or SEQ ID NO:2, wherein said sequence initiates transcription in a plant cell.

27. The method of claim 26, wherein said plant cell is from a monocot.

28. The method of claim 27, wherein said monocot is maize.

29. The method of claim 26, wherein said plant cell is from a dicot.

30. The method of claim 26, wherein the heterologous nucleotide sequence of interest encodes a gene product that confers herbicide, salt, pathogen, drought, cold, or insect resistance.

31. A method for selectively expressing a nucleotide sequence in a plant root, said method comprising introducing into a plant cell an expression cassette, and regenerating a transformed plant from said plant cell, said expression cassette comprising a promoter and a heterologous nucleotide sequence operably linked to said promoter, wherein said promoter comprises a nucleotide sequence selected from the group consisting of:
   a) a nucleotide sequence comprising the sequence set forth in SEQ ID NO:1 or SEQ ID NO:2;
   b) a nucleotide sequence comprising a plant promoter sequence that comprises at least 800 contiguous nucleotides of the plasmids deposited as Patent Deposit No. PTA-5126; and
   c) a nucleotide sequence comprising at least 800 contiguous nucleotides of the sequence set forth in SEQ ID NO:1 or SEQ ID NO:2, wherein said sequence initiates transcription in a plant cell.

32. The method of claim 31, wherein expression of said heterologous nucleotide sequence of interest alters the phenotype of said plant.

33. The method of claim 31, wherein said plant is a monocot.

34. The method of claim 33, wherein said monocot is maize.

35. The method of claim 31, wherein said plant is a dicot.

36. The method of claim 31, wherein the heterologous nucleotide sequence of interest encodes a gene product that confers herbicide, salt, pathogen, drought, cold, or insect resistance.

* * * * *

UNITED STATES PATENT AND TRADEMARK OFFICE
CERTIFICATE OF CORRECTION

| | | |
|---|---|---|
| PATENT NO. | : 7,411,112 B2 | Page 1 of 1 |
| APPLICATION NO. | : 10/961629 | |
| DATED | : August 12, 2008 | |
| INVENTOR(S) | : Diehn et al. | |

It is certified that error appears in the above-identified patent and that said Letters Patent is hereby corrected as shown below:

Column 38

Line 4: "24. The method of claim 20," should read --24. The method of claim 23,--

Signed and Sealed this

Twenty-fifth Day of November, 2008

JON W. DUDAS
*Director of the United States Patent and Trademark Office*